(12) United States Patent
Viskovich et al.

(10) Patent No.: US 11,164,666 B2
(45) Date of Patent: Nov. 2, 2021

(54) SYSTEM AND METHOD FOR REWARDING HEALTHY BEHAVIORS AND EXCHANGING HEALTH RELATED DATA

(71) Applicants: Paul Viskovich, Los Angeles, CA (US); Simon Jones, Irvine, CA (US)

(72) Inventors: Paul Viskovich, Los Angeles, CA (US); Simon Jones, Irvine, CA (US)

( * ) Notice: Subject to any disclaimer, the term of this patent is extended or adjusted under 35 U.S.C. 154(b) by 705 days.

(21) Appl. No.: 15/990,482

(22) Filed: May 25, 2018

(65) Prior Publication Data

US 2019/0362826 A1 Nov. 28, 2019

(51) Int. Cl.
| | |
|---|---|
| *G06Q 30/00* | (2012.01) |
| *G16H 20/00* | (2018.01) |
| *H04L 9/14* | (2006.01) |
| *G06Q 30/02* | (2012.01) |
| *G06Q 20/36* | (2012.01) |
| *G06Q 20/06* | (2012.01) |
| *H04L 9/30* | (2006.01) |

(Continued)

(52) U.S. Cl.
CPC .......... *G16H 20/00* (2018.01); *G06Q 20/065* (2013.01); *G06Q 20/36* (2013.01); *G06Q 30/0214* (2013.01); *G06Q 30/0222* (2013.01); *G06Q 30/0239* (2013.01); *G16H 20/60* (2018.01); *G16H 20/70* (2018.01); *H04L 9/14* (2013.01); *H04L 9/30* (2013.01); *G06Q 2220/00* (2013.01)

(58) Field of Classification Search
None
See application file for complete search history.

(56) References Cited

U.S. PATENT DOCUMENTS

| | | | | |
|---|---|---|---|---|
| 2018/0117447 A1* | 5/2018 | Tran | ........................ | G16H 10/60 |
| 2018/0248981 A1* | 8/2018 | Salem | ..................... | G16H 20/13 |
| 2018/0294047 A1* | 10/2018 | Hosseini | ................ | G16H 15/00 |

(Continued)

FOREIGN PATENT DOCUMENTS

JP 2018181345 A * 11/2018 ........... G06Q 20/065

OTHER PUBLICATIONS

Tori Adams. Blockchain, Smart Contracts, and Health: Booz Allen Hamilton and the Blockchain Revolution. (Dec. 11, 2015). Retrieved online Feb. 11, 2021. https://www.linkedin.com/pulse/blockchain-smart-contracts-health-booz-allen-hamilton-tori-adams (Year: 2015).*

*Primary Examiner* — James A Reagan
(74) *Attorney, Agent, or Firm* — Olivo IP Law Group, P.C.; John W. Olivo, Jr.

(57) ABSTRACT

The disclosed systems and methods improve on the current landscape surrounding rewards for healthy behaviors, creates a social community around various stakeholders in the healthcare system and implements discussions around preventative medicine and healthy lifestyles. Using either a traditional network or decentralized architecture, the present system creates a community around all stakeholders and facilitates recommendations and rewards in exchange for targeted lifestyle changes, such as modifications to diet, exercise, nutrition, lifestyle, psychology, rest management, hydration, and the inclusion of vitamins and supplements. The present invention further incorporates a third party marketplace that provides incentives to patient communities for accessing information and taking active steps towards living a healthier life.

43 Claims, 11 Drawing Sheets

(51) Int. Cl.
*G16H 20/70* (2018.01)
*G16H 20/60* (2018.01)

(56) References Cited

U.S. PATENT DOCUMENTS

| | | | |
|---|---|---|---|
| 2018/0307859 A1* | 10/2018 | LaFever | G16H 10/60 |
| 2019/0012660 A1* | 1/2019 | Masters | G06Q 20/381 |
| 2019/0051144 A1* | 2/2019 | David | G08B 21/0272 |
| 2019/0088373 A1* | 3/2019 | Sarmentero | G16H 50/70 |
| 2019/0096534 A1* | 3/2019 | Joao | G16H 15/00 |
| 2019/0206536 A1* | 7/2019 | Hausman | H04L 9/3226 |
| 2019/0358515 A1* | 11/2019 | Tran | A42B 3/0433 |
| 2019/0362826 A1* | 11/2019 | Viskovich | G06Q 50/22 |
| 2020/0402629 A1* | 12/2020 | Austring | G06Q 20/3678 |

* cited by examiner

SYSTEM AND METHOD FOR REWARDING HEALTHY BEHAVIORS AND EXCHANGING HEALTH RELATED DATA

BACKGROUND

Modern preventative medicine provides a method to attack and reduce many diseases such as diabetes, obesity, and heart disease. However, the healthcare system has failed to find a way to incorporate this preventative approach. As a result, even in the face of modern preventative medicine, healthcare costs continue to grow.

Much of the problem revolves around the fact that members of the healthcare process, including patients, communities, families, payers, and clinicians are disconnected entities which lack the means to collaborate to influence the actions of individuals and incorporate preventative medicine. Moreover, the issue is further compounded by the fact that the healthcare payment model is opaque since it excludes physicians, patients and their support networks from participating in incentivizing healthy behavior.

Previous attempts to give power back to patients and reward healthy behavior have failed for several reasons. The present invention seeks to resolve those issues through the decentralized network, virtual currency, and a social economy. In particular, the present invention utilizes a decentralized platform to connect all stakeholders, disburse relevant information, and reward healthy behavior in order to create a community that can implement preventative medicine into patients' lives.

SUMMARY

Patients, their families, healthcare providers, payers and clinicians (collectively, "Stakeholders") play a significant role in the financial and clinical outcomes of healthcare. Yet todays healthcare systems fail to engage these Stakeholders to reward the actions necessary to improve the healthcare system. Studies have shown that an estimated 40% of premature deaths in the U.S. are due to modifiable behavior. However, once a patient leaves a healthcare facility, Stakeholders become disconnected from each other and lack the necessary tools to educate, motivate, and incentivize the right behaviors.

Previous solutions attempted to resolve these issues by providing a reward system for healthy behavior. For example, medical plans provided a method to reduce the costs of monthly health benefits by rewarding exercise or healthy behavior. However, studies have proven that such healthy behavior was only temporary with limited results, since Patients only participated in such programs for short periods of time.

In addition, while rewarding diet and exercise could be beneficial, previous methods failed to account for the need for customized healthcare. Cultural backgrounds, dietary restrictions, genetic factors all impact the behavior of certain individuals. Since previous approaches were generalized, they failed to use the statistical measures available to reward healthy behavior that may be more important to specific individuals.

For example, previous inventions disclose a method to reward specific behaviors, such as weight loss. However, such a reward fails to prioritize whether weight loss is the best behavior for all individuals: consider a 35-year-old male who is a practicing vegetarian. This individual may be living a healthier lifestyle by incorporating specific proteins or vitamins into their diet instead of losing weight. Such targeted information would only be in the possession of clinicians who are excluded from the process. Moreover, one 35-year-old male who is a practicing vegetarian may know which vitamins and proteins are beneficial, while another may not have the same information.

Another issue fragmenting the healthcare system is the fact that the tools necessary to improve change are not readily available in a connected marketplace. Currently, a Patient that may benefit from certain vitamins or dietary changes must seek out or learn that information, then seek out or learn the treatment, then finally find a way to incorporate the treatment into their daily lives. The healthcare system does not provide additional rewards for such a behavior.

The present invention seeks to provide and share relevant information to all Stakeholders through a decentralized social platform. By using a decentralized digital ecosystem, targeted information can be accessed, recommended, and shared amongst all individuals who participate in the network. Finally, by connecting healthcare payers, providers, and patients, in a decentralized manner forms a feasible solution to reward each for their value added to the system. Additionally, and importantly each stakeholder on the decentralized system is able to set and provide rewards to any other stakeholder on the system. This departure from previous methods of providing rewards through a centralized body (such as airline frequent flier miles) allows for broader participation and creation of a "rewards economy". Through broad participation in the "rewards economy" with stakeholders able to earn and redeem rewards from each other allows tailored incentives that provide significantly greater motivation and value to each stakeholder in the system. Such information can motivate and incentivize all Stakeholders to enact long term healthcare changes.

In one embodiment of the present invention, the decentralized network is a blockchain network. Blockchain technology (sometimes simply referred to as a blockchain) was developed and has been used in certain digital currency implementations. An example implementation and corresponding blockchain techniques are described in a 2008 article by Satoshi Nakamoto, called "Bitcoin: A Peer-to-Peer Electronic Cash System," the entire contents of which are hereby incorporated by reference. With that being said, in certain embodiments discussed herein, the blockchain may be privately hosted (e.g., where all member nodes are run and provided by the same entity or a controlled group of entities). In certain example embodiments, the blockchain may be a distributed blockchain, such as the one provided by the bitcoin network. Thus, the term blockchain as used herein is not confined to the so-called blockchain that is only used for the bitcoin cryptographic currency.

The blockchain is a data structure that stores a list of transactions and can be thought of as a distributed electronic ledger that records transactions between source identifier(s) and destination identifier(s). Every transaction is "to" a destination identifier that is associated with a public/private key pair. In creating a new transaction, outputs from other, prior transactions that are to the "from" address (which may be multiple different addresses derived from the same private key) are used as inputs for this new transaction. The new transaction is then encumbered with the public key associated with the "to" destination identifier. In other words, outputs from prior blockchain transactions are used as inputs for new transactions that are then signed using the public key associated with the destination address. The new blockchain transaction is then submitted to the blockchain. Once on the blockchain multiple such transactions are bundled into a block and the block is linked to a prior block in the "blockchain." Computer nodes of the distributed system then maintain the blockchain and validate each new block (along with the transactions contained in the corresponding block). The techniques described herein make use of blockchain technology to address one or more problems with the conventional database systems to provide a pooled resource for publishers and advertisers.

Specifically, through the use of a traditional network or a decentralized blockchain network, Patient data can be analyzed in conjunction with healthcare issues associated with specific individuals and rewards provided from any stakeholder to any other stakeholder. Healthcare providers can pool historical data to determine patterns and modifiable health actions that will best benefit individuals.

Data security in a blockchain network is further increased by implementing it on a distributed decentralized network. This means a large number of users all have access to the blockchain and are all attempting to add blocks to the end of the chain by either finding a nonce that produces a valid hash for a given block of data or creating a majority consensus that previous blocks and transactions are valid. Blockchains on a distributed decentralized network with sufficiently restrictive rules for creating valid blocks are fairly secure against unauthorized changes to the data stored in them.

In certain embodiments, a distributed decentralized network interacts with a blockchain. As described, the system advantageously provides cryptographically safe storage and immutability for the records that are stored on the blockchain. This is especially important when considering the sensitive nature of patient and healthcare data. The system allows for a complete history of transactions (e.g., a chain of transactions). In certain example embodiments, cryptographic signing may be required or used to facilitate the transfer or issuance of data.

The use of the blockchain requires consensus confirmation of submitted transaction before they may be considered "committed" to the cryptographic ledger that is represented by the blockchain. The records on the blockchain then provide a shared view of data derived from a marketplace across all business stakeholders (e.g., network administrators, users, publishers, advertisers, Patients, Clinicians, Payers, miners, data analysts, etc.). In certain example embodiments, the use of the blockchain to store Patient data and healthcare data may provide for an agreed upon view (or record) of trades and positions between multiple different computer systems. Such an implementation may thus decrease the cost of replication across databases.

When conventional database techniques are used in online database systems, it may be difficult to efficiently distribute the information contained within the database across the multiple different parties. In particular, when databases are distributed in such a manner, reconciliation may become a problem (e.g., keeping the database in sync with each other). In those types of distributed environments, it can be difficult to determine which database has the "correct" version of the data if there is a discrepancy between the different database locations. The problem becomes even more evident where there are multiple different entities that must interact with the database. Signing of transactions may not be performable in an STP manner and/or a consensus process for confirmation of those transactions across several parties may be infeasible (if not outright impossible). One or more of these technical issues may be addressed by storing objects (e.g., asset classes, trades, positions, collaterals, etc.) on a blockchain (e.g., within the same ledger). Additionally, use of traditional database technology to log transactions enforces centralization/control of the data input. This limits the ability for stakeholders on the system to transact with each other unless the transaction types have been previously imagined and approved by the central body controlling the database.

In another embodiment, all members will have access to the relevant information needed. Patient data will be collected and analyzed for health risks and health patterns. Recommended behavioral changes will be automatically made and provided to the Patient's specific healthcare provider, payer, and other specified Stakeholders. Additional third parties may participate in the rewards system, by marketing and selling healthy products through the network.

Each participating member can be rewarded by any other member for their participation in the network by providing personal data, or solutions. Payers will be incentivized to participate, since they can easily track the best methods to reduce healthcare costs and improve profitability.

The technical features described herein may thus improve the security, verifiability, and reliability of trade information for one (or more) online advertising using historical data.

BRIEF DESCRIPTION OF THE DRAWINGS

Embodiments of the invention are described in detail below with reference to the drawing figures, which form a part of this disclosure, and are incorporated by reference herein, and wherein.

DETAILED DESCRIPTION OF THE PREFERRED EMBODIMENT

The advent of preventative medicine has allowed a method by which persons can live a healthier lifestyle and reduce healthcare costs. However, the healthcare system has not found a way to reward healthy behavior or incorporate all stakeholders in the healthcare process. Such healthy behavior has included, without limitation, modifications to diet, exercise, nutrition, lifestyle, psychology, rest management, hydration, supplements, and other related modifications. The present embodiment provides a method Payers, Healthcare Providers, Patients, Advertisers, Families, Employers, Caregivers, etc. ("Stakeholders") and their Communities into one network, and track healthy behaviors. Moreover, the present invention teaches a method to allow any Stakeholder to recommend and reward any other Stakeholder for healthy behavioral changes.

The present invention further provides a reward for healthy behaviors. As a method for enacting lasting change, a reward can be provided to any of the stakeholders for applying methods to deploy preventative medicine. Such changes can be recommended by any Stakeholder, to any Stakeholder. Rewards can be distributed by any Stakeholder, or autonomously through the system. Payers will be incentivized by the declining cost of healthcare, while care providers will be incentivized by the reward system. Patients and their families will be further incentivized by the reward system and a better lifestyle.

The system itself will provide a method of connecting a network of connected users ("The Network"). The Network will require at least one server, a processor, and networking interfaces. Such a Network will allow the connection of user devices through the Internet. The Network itself will consist of at least one server, which will host a webpage, that when executed, will allow users to access a portal and be identified cryptographically using a private key and public key. The web portal or other network connected device will provide a social platform to connect a patient circle, with their respective payer circle, and their care providers. The patient's health and data will be tracked and stored on the server. The rewards engine will track any behavior recommendations, and issue rewards accordingly.

Figure 1:
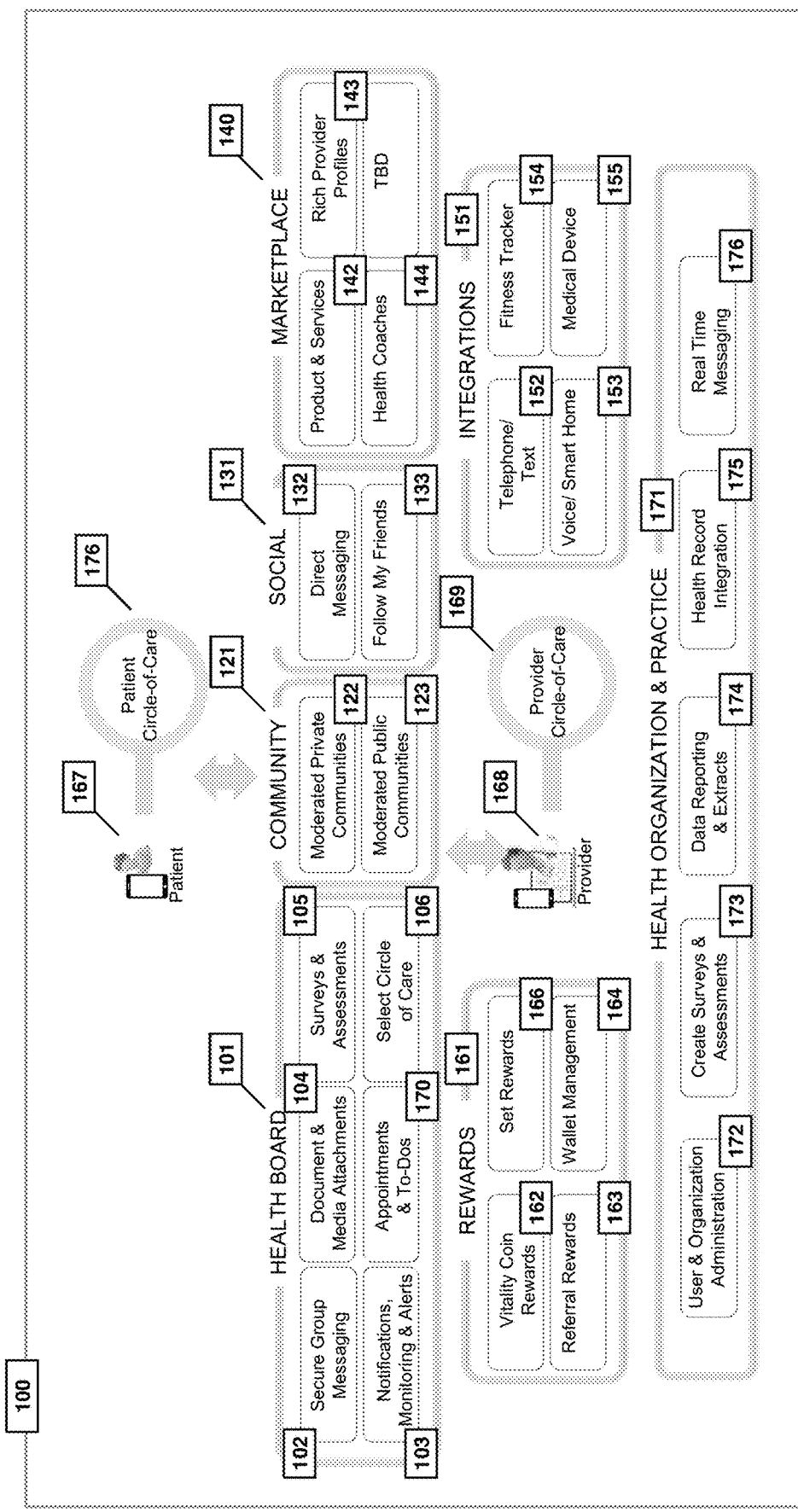
FIG. 1 depicts a block diagram illustrating one embodiment of the current invention.

With reference to FIG. 1, a diagram generally illustrating this method is provided and referenced with the numeral 100. Each of the Stakeholders (including care providers, patients, payers, etc.) will be connected through various circles to various stakeholders, such as their friends 132, and their provider 123. The system will provide various features including secure group messaging, 102, Document and media attachments 101, notifications and alerts, 103, and a circle of care 106. The community may feature other information such as private forums 122, and moderated online discussion portals 121. The members may have access to a direct messaging system 131, and a Marketplace 140, featuring Products and Services 142, Provider profiles 143, Health Coaches 144, and other related features.

Through this Network, Providers will have a secure method of creating Telephone or text message contacts 152, track a Patient's fitness through wearable devices 154, and other smart home 154 or medical device integrations 155.

Stakeholders can be rewarded for implementing healthier lifestyle and behavioral decisions through virtual currency, such as a VitalityCoin 162. The rewards can be pre-set or automatically generated 163, referred by any other Stakeholder, including other providers or payers 165, and managed in a digital wallet 164. Many of these features can be further modified, as described in detail below. FIG. 1 further incorporates Appointments & To-Dos 170, Patients 167, Set rewards 166, The provider 168, the provider circle of care 169, Health Organization and Practice 171, User and organization administration 172, Creation of Surveys and Accessories 173, Data reporting and Extracts 174, Health Record Integration 175, and real time monitoring 176.

The system itself will allow the Network to connect to at least one data storage unit containing data that can be processed ("Data Storage and Analysis Server"). The Data Storage and Analysis Server will have the ability to collect and analyze data regarding the various Stakeholders, which will be furthered to a rewards engine. The rewards engine will be executed to set, distribute, and report regarding healthier behavior recommendations, and the associated rewards.

Figure 2:
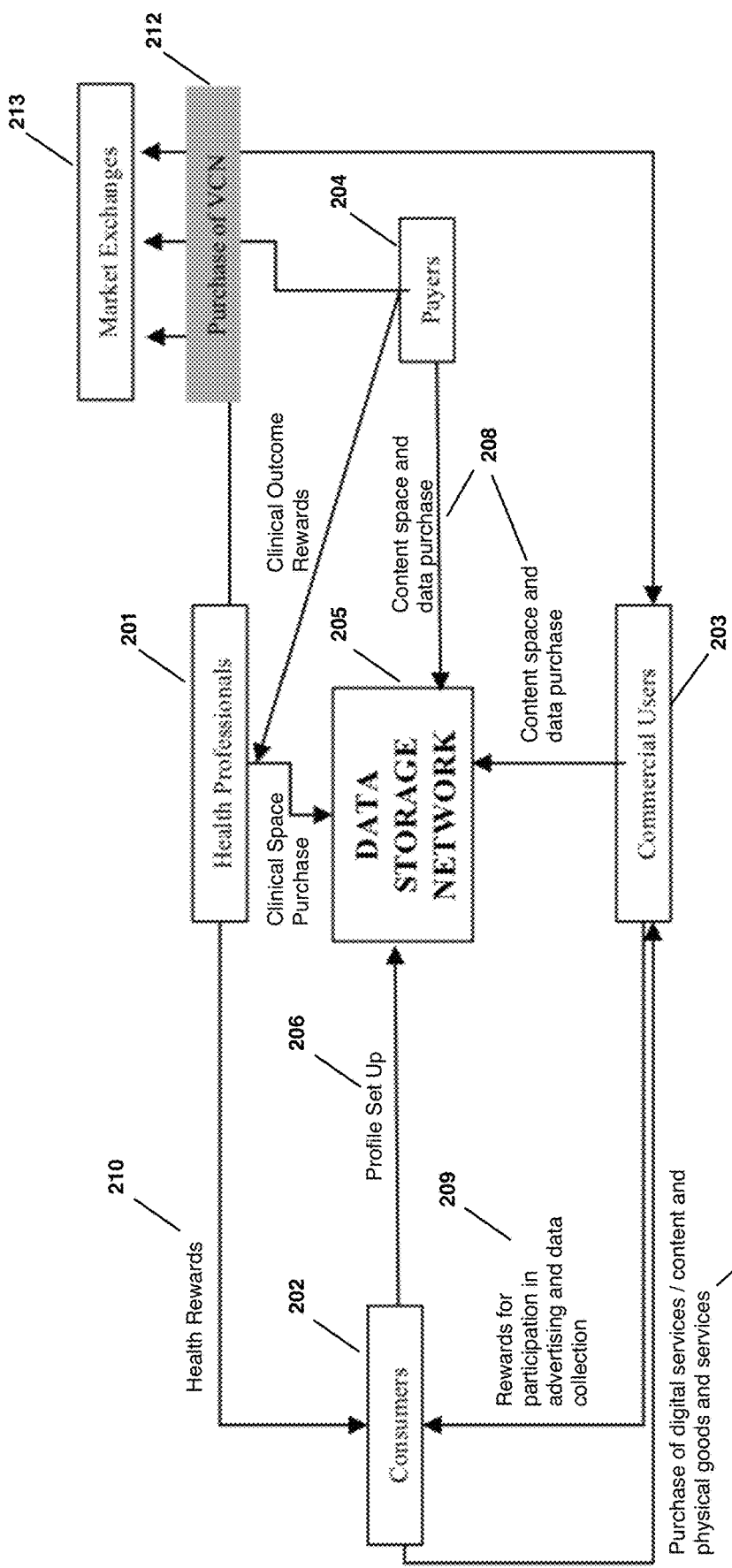
FIG. 2 depicts a block diagram illustrating one embodiment of the current invention.

FIG. 2, generally represented by the numeral 200, depicts one embodiment of the present invention, Stakeholders, such as Consumers, 202, Commercial Users 203, Health Professionals 201, and Payers 204, can be connected on a Data Storage Network 205. Each of these Stakeholders will have a profile 206, purchase clinical space 207, and can further purchase content space or data 208. In this embodiment, Stakeholders, including without limitation, Health Professionals 201, can reward 210 consumers 202 directly for healthy behavior. In addition, Commercial Users 203 can reward consumers for providing access to data 209. Consumers will further have the option to purchase services and goods through a marketplace 211 serving the Commercial Users 203. FIG. 2 further depicts a Market Exchange 213 and the ability to purchase a token such as VCN 212.

In another embodiment, third party providers of products and services can purchase advertising space, or avenues to connect directly with Stakeholders. Stakeholders can be incentivized to adopt healthy behaviors recommended or advertised by third party providers.

The Network itself can be a centralized (Traditional) or Decentralized (Modern) system. A disadvantage of the Traditional method is that it is difficult to connect all Stakeholders in the system, since the Traditional method relies on a fortified central server that is managed by a third party and accessible by all members that can create an account on said system.

A decentralized system provides a distinct advantage, in that it allows all Stakeholders to participate in an unmanaged network with relative ease. Since all Stakeholders with accounts are interconnected on a decentralized system, transactions become easier as well.

In one embodiment, the Network is made up of a plurality of nodes, each node connected to another node in the plurality of nodes, having the ability to pass data to each of the connected plurality of nodes. At least one node of the plurality of nodes is connected to an existing blockchain. Using this existing blockchain the, decentralized transactions can take place.

In one embodiment, each transaction (or a block of transactions) is incorporated, confirmed, verified, included, or otherwise validated into the blockchain via a consensus protocol. Consensus is a dynamic method of reaching agreement regarding any transaction that occurs in a decentralized system. In one embodiment, a distributed hierarchical registry is provided for device discovery and communication. The distributed hierarchical registry comprises a plurality of registry groups at a first level of the hierarchical registry, each registry group comprising a plurality of registry servers. The plurality of registry servers in a registry group provide services comprising receiving client update information from client devices, and responding to client lookup requests from client devices. The plurality of registry servers in each of the plurality of registry groups provide the services using, at least in part, a quorum consensus protocol.

As another example, a method is provided for device discovery and communication using a distributed hierarchical registry. The method comprises Broadcasting a request to identify a registry server, receiving a response from a registry server, and sending client update information to the registry server. The registry server is part of a registry group of the distributed hierarchical registry, and the registry group comprises a plurality of registry servers. The registry server updates other registry servers of the registry group with the client update information using, at least in part, a quorum consensus protocol.

As another example, a computer-readable medium comprising computer executable instructions for causing a client device to perform a method for device discovery and communication is provided, the method comprising broadcasting a request to identify a registry server, receiving a response from a registry server, and sending client update information to the registry server. The registry server is part of a registry group of the distributed hierarchical registry, where the registry group comprises a plurality of registry servers. The registry server updates other registry servers of the registry group with the client update information using, at least in part, a quorum consensus protocol.

In some embodiments, the system is further able to conserve network and computing resources by securely storing information associated with user data, preventing potential malicious activity involving such information, conserving bandwidth, memory, and computation resources.

A digital wallet is software and hardware (or specifically designed hardware) that allows an individual to make electronic commerce transactions that use, a blockchain. The digital wallet is a data structure that can include a private key (e.g., that is only known to the holder of the wallet) and a series of identifiers (sometimes called wallet identifiers, blockchain identifier, or walletIDs herein) that have been generated based on the private key. These identifiers are used to allow other users to "send" transactions, which are recorded on the blockchain, to that identifier. For example, the above novation process creates two blockchain transactions for a trade between Publisher ("Party A") and the distributed decentralized network administrator ("Party B"). A first blockchain transaction may be from the wallet of party A to the wallet of the Party B. A second blockchain transaction may be from the wallet of the Party B to a wallet of party A. These transactions may be separately generated and submitted to the blockchain. Alternatively, the blockchain may only have one "wallet" that is being used for interacting with the blockchain. Other types of implementations may also be possible (e.g., where different parties, or their respective computer systems, use their own keys for a central blockchain). In certain embodiments, the wallets may be centrally managed by the distributed decentralized network computer system that the parties associated with the trade. However, the transactions recorded to the blockchain may still be signed by or otherwise associated with the individual wallets of the respective publishers.

In certain example embodiments, a generated blockchain transaction may include a so-called smart contract. As used herein, smart contracts are computer programs or scripts (e.g., programmatic structures) that are embedded into or externally execute blockchain transactions that are executed on the blockchain (e.g., distributed system and/or the nodes thereof). A simple example of a smart contract may be software program that automatically sends 10 dollars (in the form of a blockchain transaction) from A (the wallet of A) to B (the wallet of B) when B can run a mile in 6 minutes. Alternatively, a smart contract may be used to calculate the total rewards for a particular Stakeholder based on the amount of rewards historically provided for certain activities the type of activity the Stakeholder is participating in. Such a smart contract would then automatically generate a transaction from the network and transfer the appropriate reward amount. In certain embodiments, each smart contract that is stored onto the blockchain may be associated with a blockchain address at which the "event" for the smart contract will be sent.

In certain example embodiments, blockchain may be directly accessed (e.g., using an appropriate blockchain protocol) by other systems (e.g., computer systems that are directly controlled the distributed decentralized network administrator), and/or other post-trade systems 138. Each of these systems may access blockchain directly, and/or via blockchain services. Other parties such as banks or exchanges may read the blockchain for the transactions thereon. Such an approach may alleviate costly replication processes because the blockchain is the central or golden record for the trades and positions with respect to the advertisement data. In certain instances, publishers access information stored on the blockchain, they may end up bypassing the traditional proprietary gateways and protocols used in other types of computer system implementations.

Particular embodiments of the present disclosure may provide some, none, or all of the following technical advantages associated with cryptocurrency transactions in exchange for advertising data. For example, in certain embodiments, the system is able to identify that the number of validations from a plurality of nodes insufficient to confirm the transaction before completing the requested cryptocurrency transaction, thereby conserving the bandwidth, memory, and computation resources consumed by correcting erroneous cryptocurrency transaction after completion.

Figure 3:
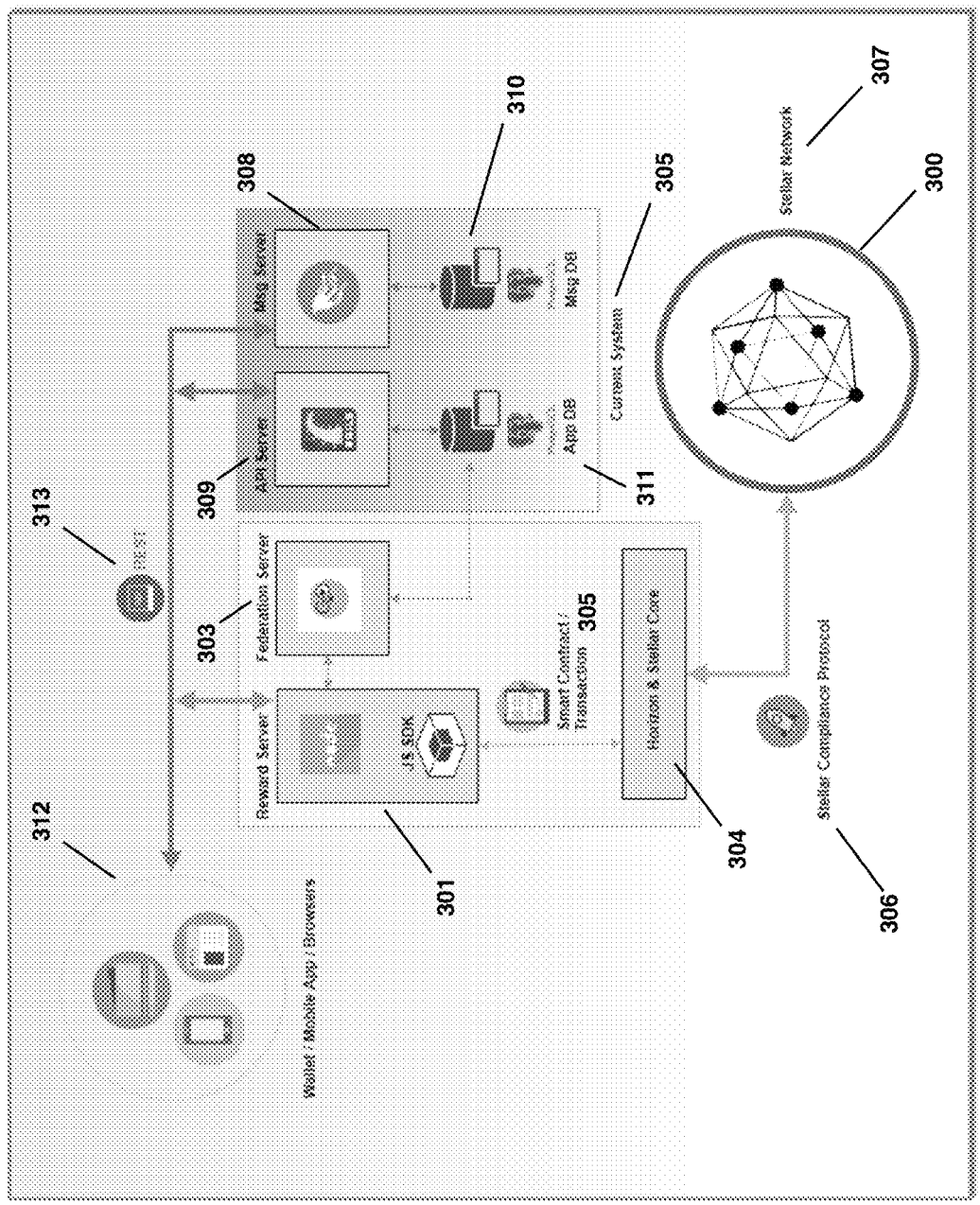
FIG. 3 depicts a diagram illustrating one embodiment of the present invention.

FIG. 3, generally marked by the numeral 300, provides an illustrative block diagram depicting a method of by which The Stellar Network can be connected to at least one node in the Network making up the present invention. The Reward Server 301, is directly connected to the Stellar Network Core 302, and the Federation Server 303, communicates with the reward server 301 to pass information from a Web Portal, or other connected device, via a smart contract 305. This allows the deployment of Smart Contracts using the Stellar Compliance Protocol 306 and on the Stellar Blockchain Network 307. The Figure further shows an Application database, or App Db 311 and a message database or Msg DB 310, and their respective API Server 309, or Msg Server 308, the rest 313 and a Wallet, Mobile App, or Browser 312.

The inclusion of a connected platform where rewards can be distributed by any player provides certain advantages. First, previously unincluded Stakeholders are incentivized to enact change in Patient Healthcare.

Figure 4:
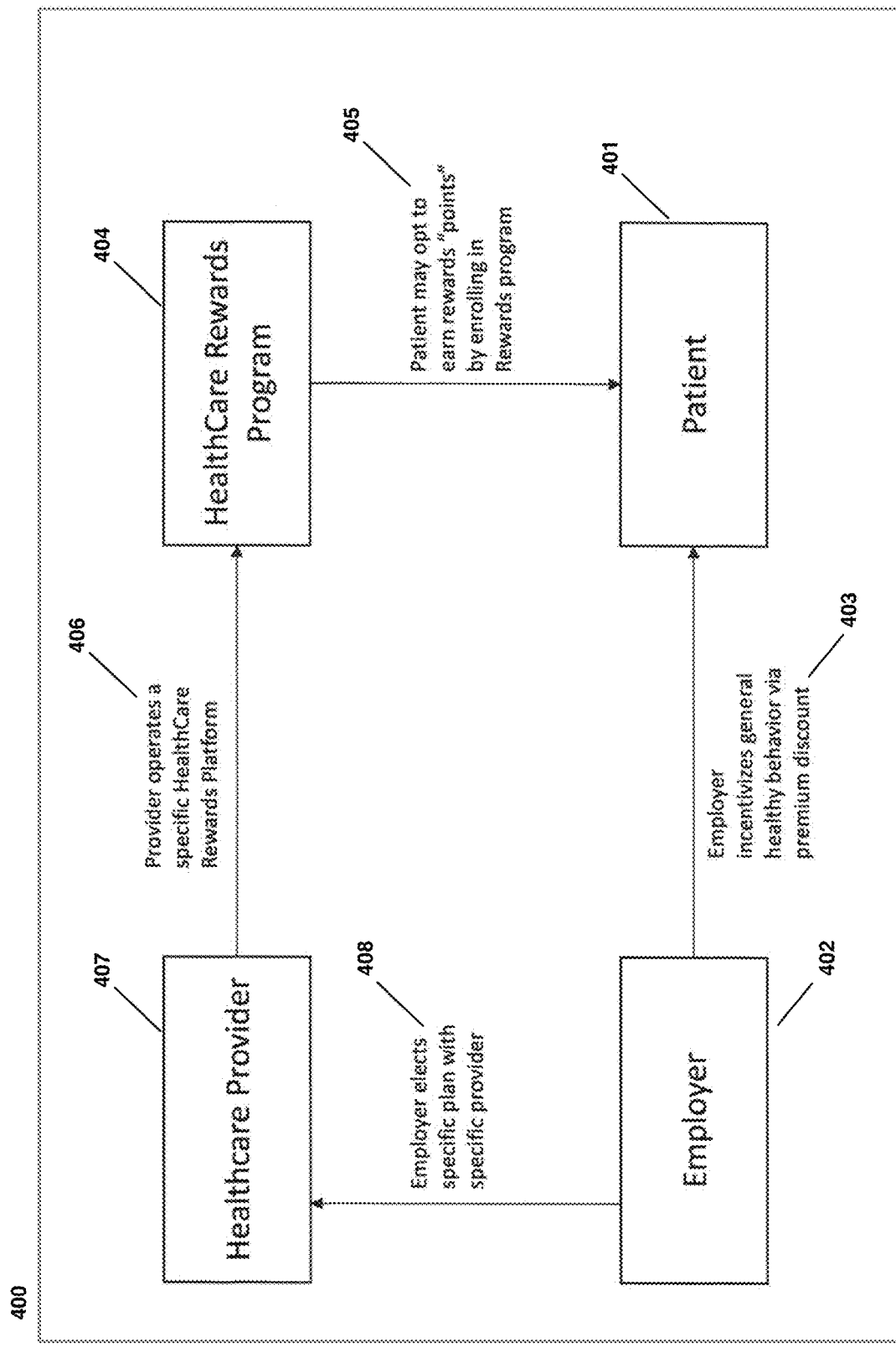
FIG. 4 depicts a block diagram illustrating the traditional approach to rewards and healthcare.

FIG. 4, which is generally represented by the numeral 400, depicts an illustrative block diagram showing certain disadvantages of the previous method. Specifically, a patient 401, has previously been incentivized to enact healthier behaviors in two methods, by an employer 402, who provides incentives through the use of healthcare premium discounts 403, or a Healthcare Rewards Program 404, which provides points for certain healthier behaviors 405. Not only is the Healthcare Rewards Program operated 406 by the HealthCare provider 407, but the employee is limited to select a program through the limited choices provided by the Employer's elected health providers 408.

Figure 5:
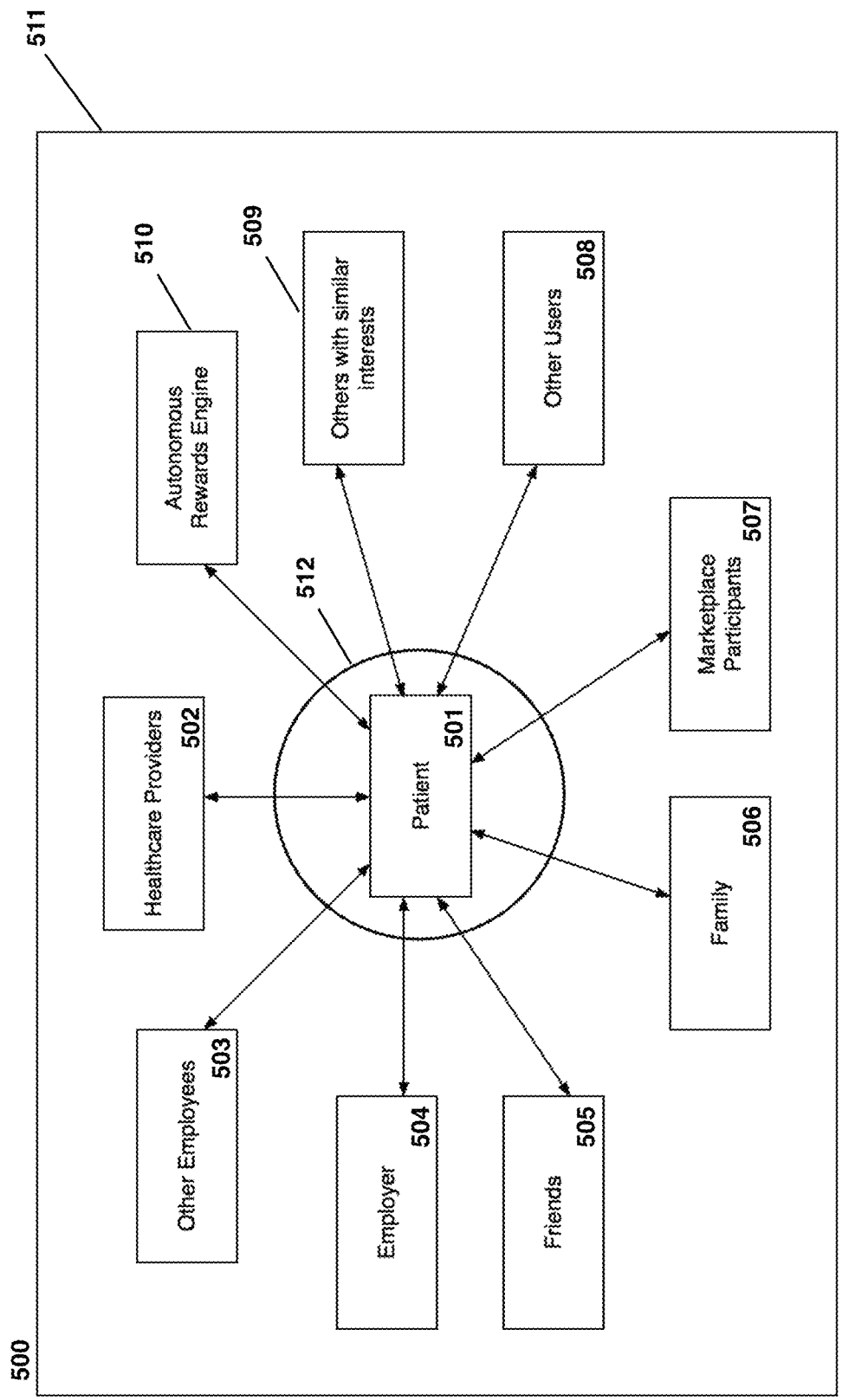
FIG. 5 depicts a block diagram illustrating the current method of decentralizing rewards and healthcare.

The proposed method democratizes or decentralizes this system to incorporate more Stakeholders in the process. FIG. 5, which is generally represented by the numeral 500, depicts an illustrative block diagram showing all the stakeholders that have access to a specific patient 501. The system 511, can be deployed in a decentralized network 512. A decentralized method provides direct access to HealthCare Providers 502, Other employees 503, Employers 504, Friends 505, Family 506, Marketplace Participants 507, Other Users 508, and Others with Similar Interests 509. An autonomous rewards engine 510, provides all Stakeholders a line of communication with each other, and method to recommend and reward specific behavior.

Figure 5A:
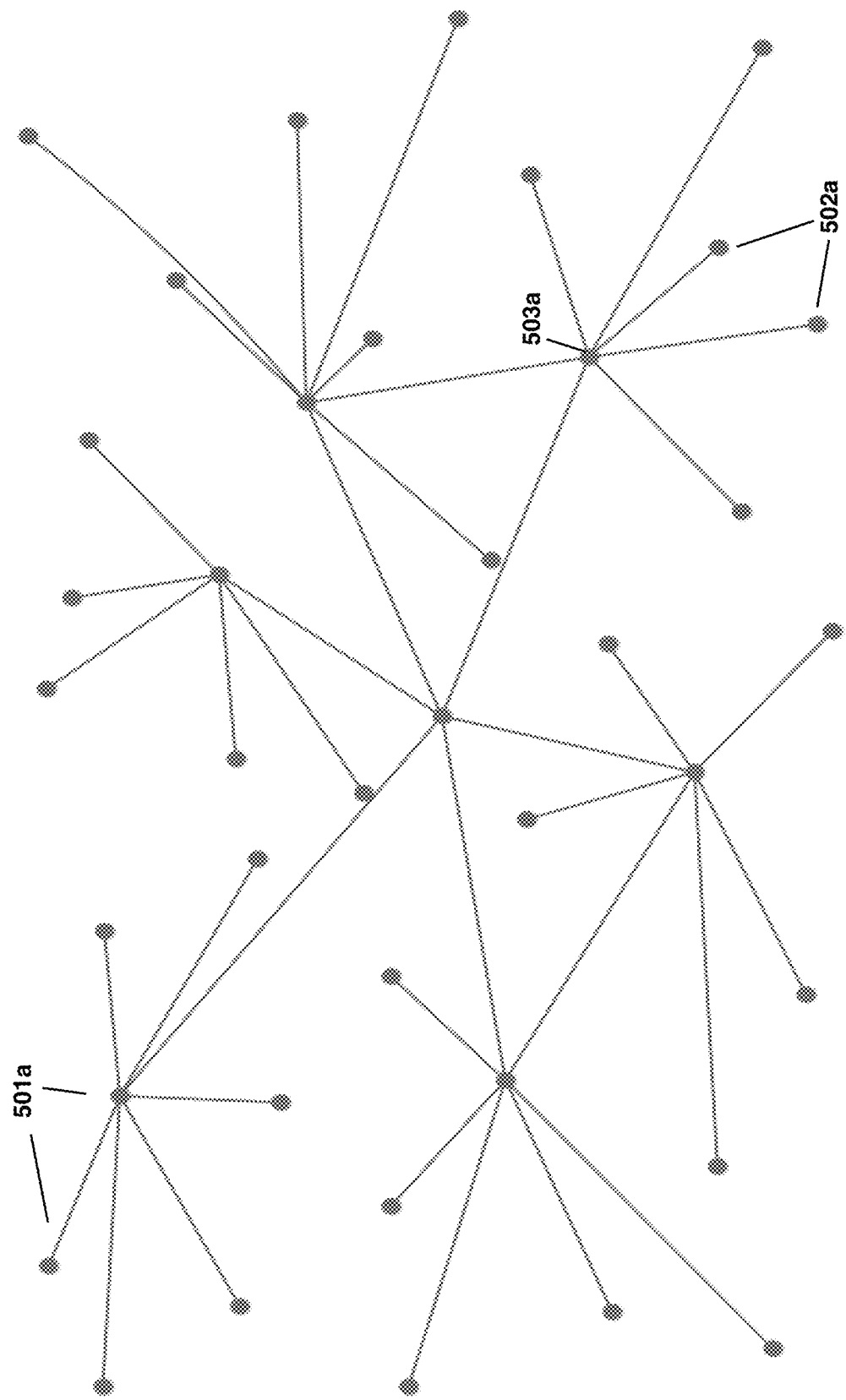
FIG. 5a is a line diagram illustrating a decentralized network.

The specific architecture of the network can be either decentralized or distributed. FIG. 5a, generally represented by the numeral 500a provides an illustrative diagram of the decentralized network. FIG. 5a depicts each node with a dot 501a. Under this system, each node is connected to at least one other node 502a. Only some nodes are connected to more than one node 503a.

Figure 5B:
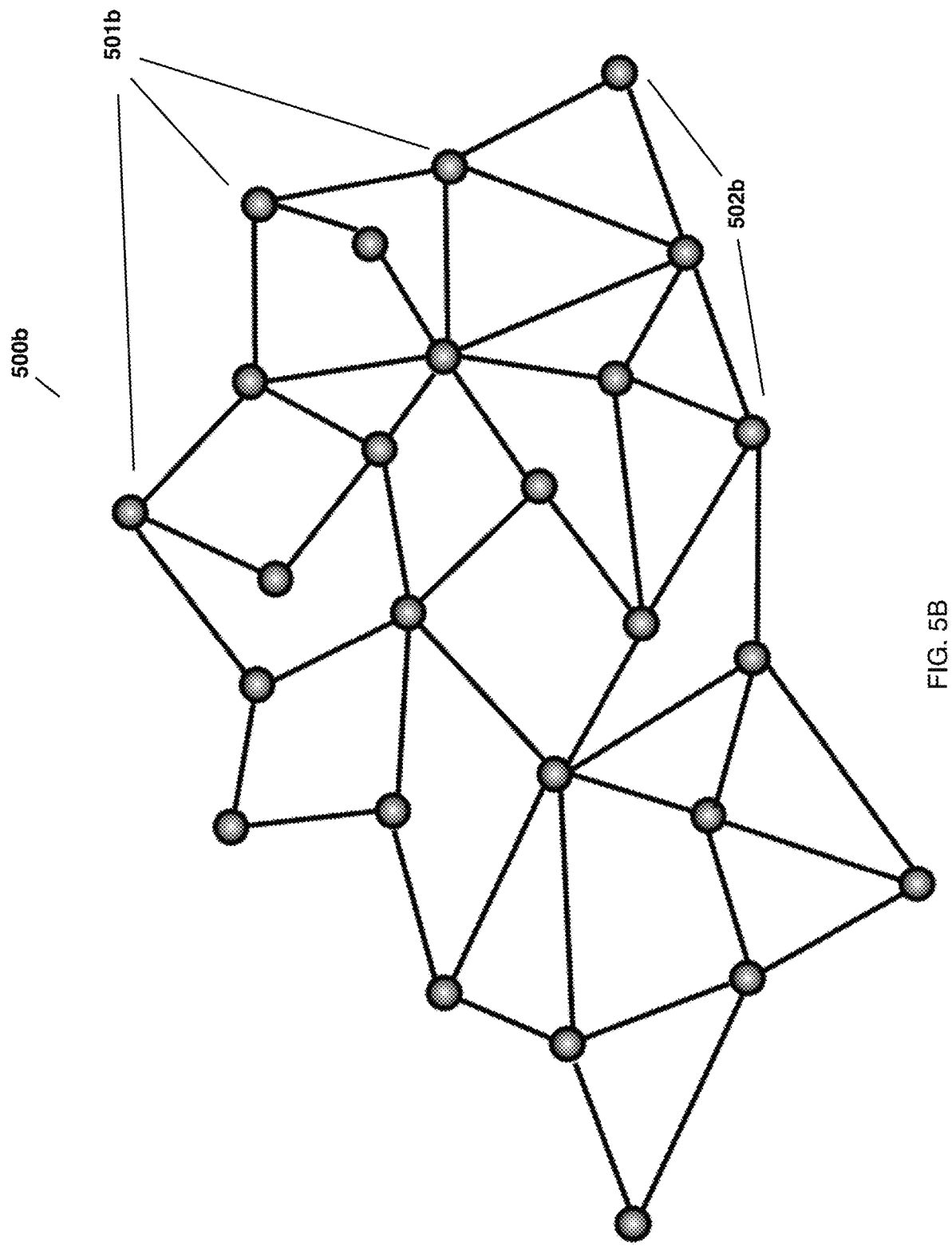
FIG. 5b. is a line diagram illustrating a distributed network.

For comparison purposes, FIG. 5b, which is generally represented by the numeral 500b, illustrates a distributed network. Each node is represented by a dot 501b. Unlike a decentralized network, each node of a distributed network is directly connected to at least two other nodes 501b. This makes it more difficult to attach a distributed network. The present invention can be deployed on a centralized, decentralized, or distributed network.

Figure 6:
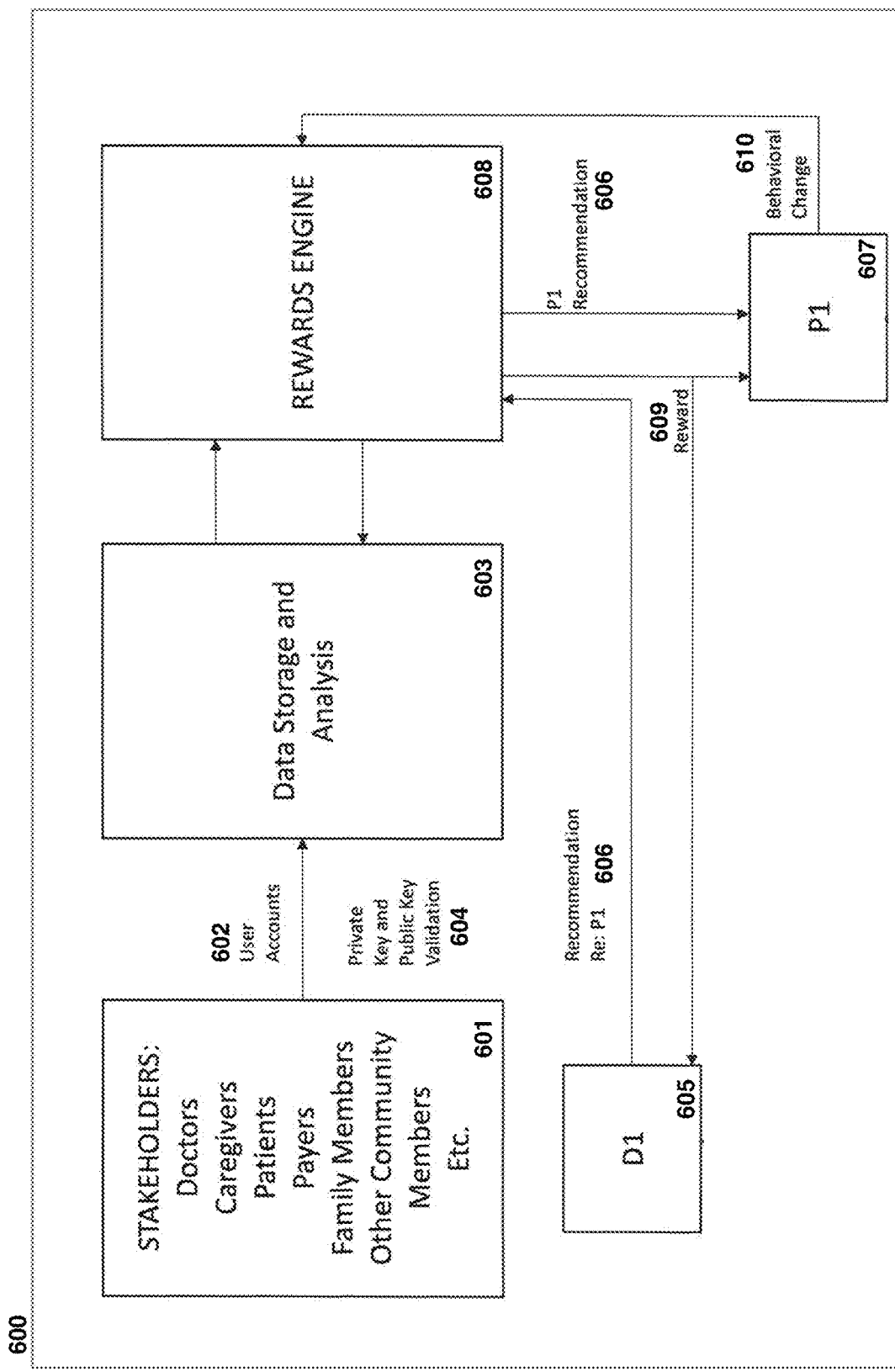
FIG. 6 depicts a block diagram illustrating one embodiment of the present invention.

FIG. 6, which is generally represented by the numeral 600, depicts an illustrative block diagram showing one embodiment in which Stakeholders are incentivized to recommend healthier lifestyles. Each of the Stakeholders 601 have a user account 602 stored in a data storage server 603. The Stakeholders can be identified and/or distinguished by a private and public key 604 associated with their account. When a care provider ("D1") 605 makes a recommendation 606 for a Patient ("P1") 607 to make a specific behavioral modification. D1's recommendation, and basis for recommendation 606 is passed to the data server 603, and then to a rewards engine 608. The rewards engine distributes that information to P1 607. Upon patient's completion of a behavior modification 610, a reward is automatically issued to the patient and the doctor 609. In addition, the recommendation information is compiled and analyzed to autonomously deploy further recommendations as described below.

In one embodiment of the present invention, any of the healthcare provider or payer can set the value of the reward based on the recommendation and activity. Another embodiment provides a method by which the rewards engine would aggregate all the recommended activities, and autonomously set the reward value. Under that scenario, the rewards would be distributed automatically by the rewards engine to the appropriate parties.

Figure 7:
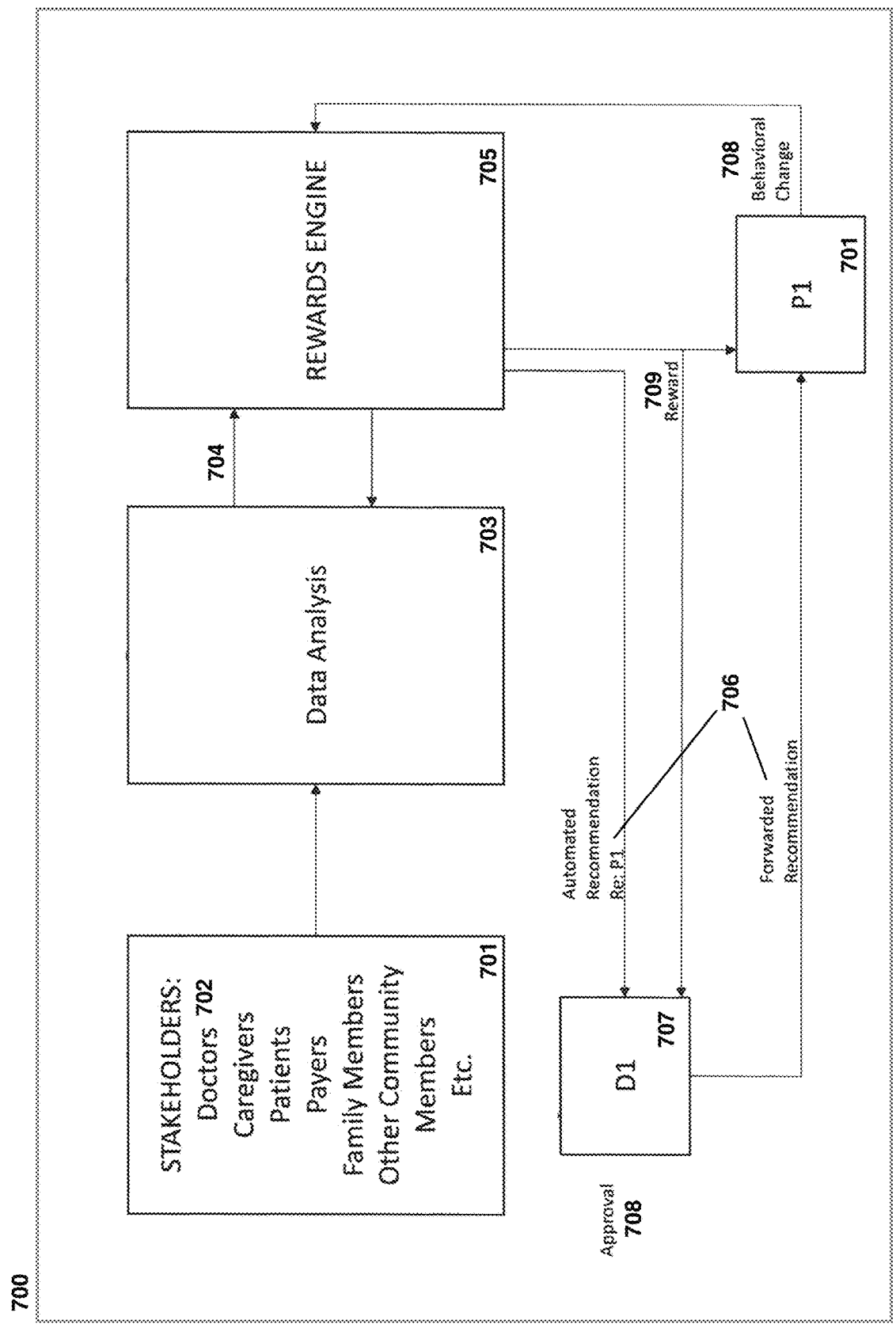
FIG. 7. depicts a block diagram illustrating one embodiment of the present invention.

FIG. 7, which is generally shown by the numeral 700, is an illustrative diagram depicting another embodiment of the present invention, wherein the Rewards Engine can autonomously recommend and deploy rewards based on healthier behaviors. Stakeholders 701 provide data including both patient data and provider recommendations, which are aggregated and analyzed b the data analysis server 703. The analyzed data 704 information is passed to the rewards engine 705, which furthers the recommendation to a caregiver 706 that has made the recommendation to a patient with similar characteristics. Upon the caregiver 702 approval 707, the patient ("P1") 707 is given the recommendation. Should the patient comply with the activity 708, a reward is distributed to the patient for the behavior modification 709.

In another embodiment, the reward can be distributed 709 to the caregiver 702 in conjunction with P1 701.

Another advantage of the present invention is that it allows patients to receive information from caregivers. It further provides a source for targeted and specialized information. Finally, it provides a method by which caregivers can provide information to various consumers.

Figure 8:
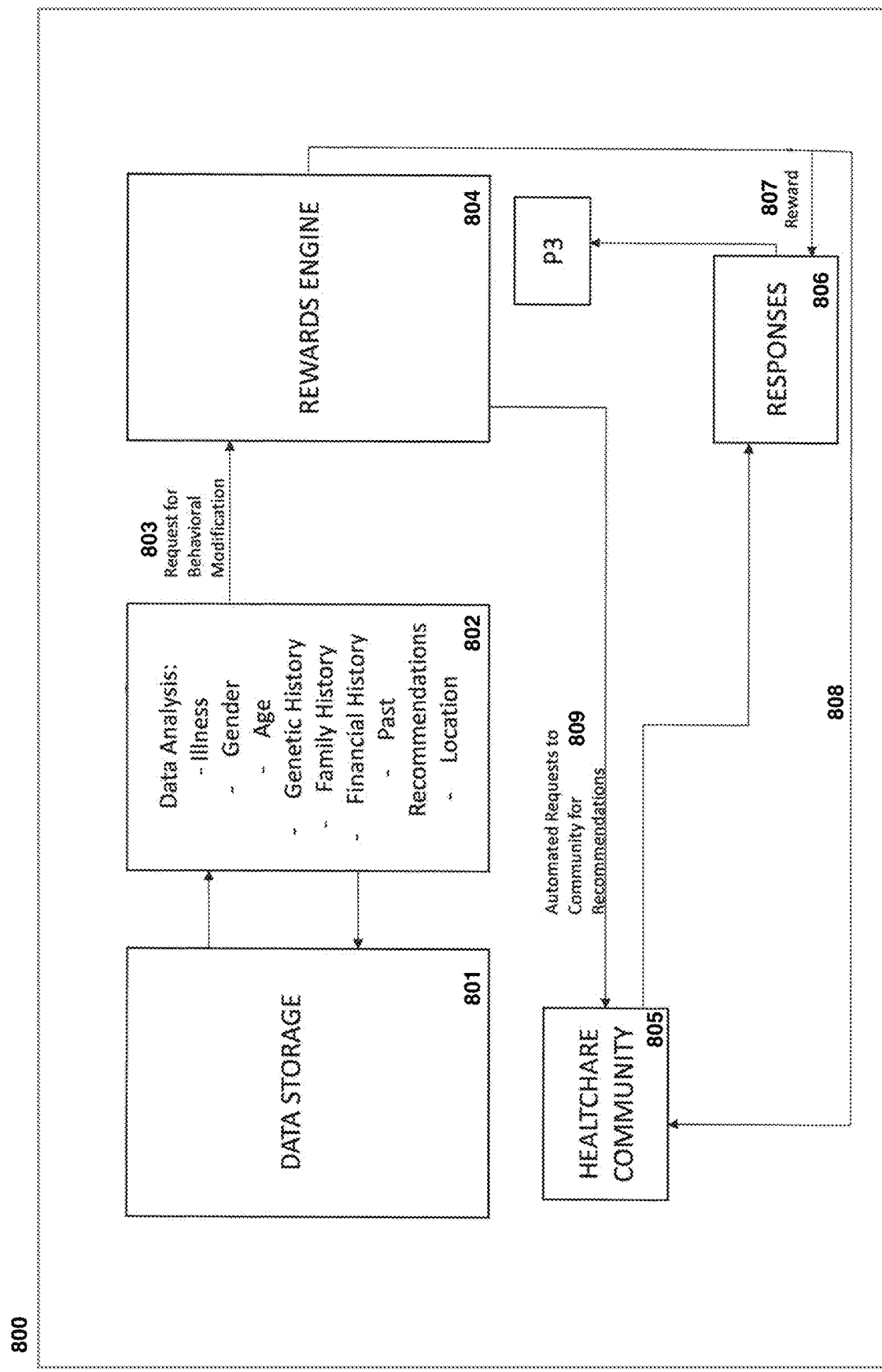
FIG. 8. depicts a block diagram illustrating one embodiment of the current invention.

FIG. 8, generally shown by the numeral 800, illustrates another aspect of the present invention. Data regarding Stakeholders such as a Caregiver 801 and Patient ("P3") 804 and recommendation data 802 can be categorized by the data storage and analysis server 803 in multiple formats. Patients can be sorted by race, gender, age, creed, and any other classifiable manner. Recommendations 809 can be analyzed from a multitude of approaches, including a patients age, genetic background, geographical location, etc.

In another embodiment, specific information regarding patient health that has been is passed to the rewards engine. The rewards engine provides that data to the clinical community at large. Care providers are requested to make recommendations and provide health guidance and literature related to specific patients. That information is further passed back to the patient community. Care providers are rewarded for providing literature and health information.

Figure 9:
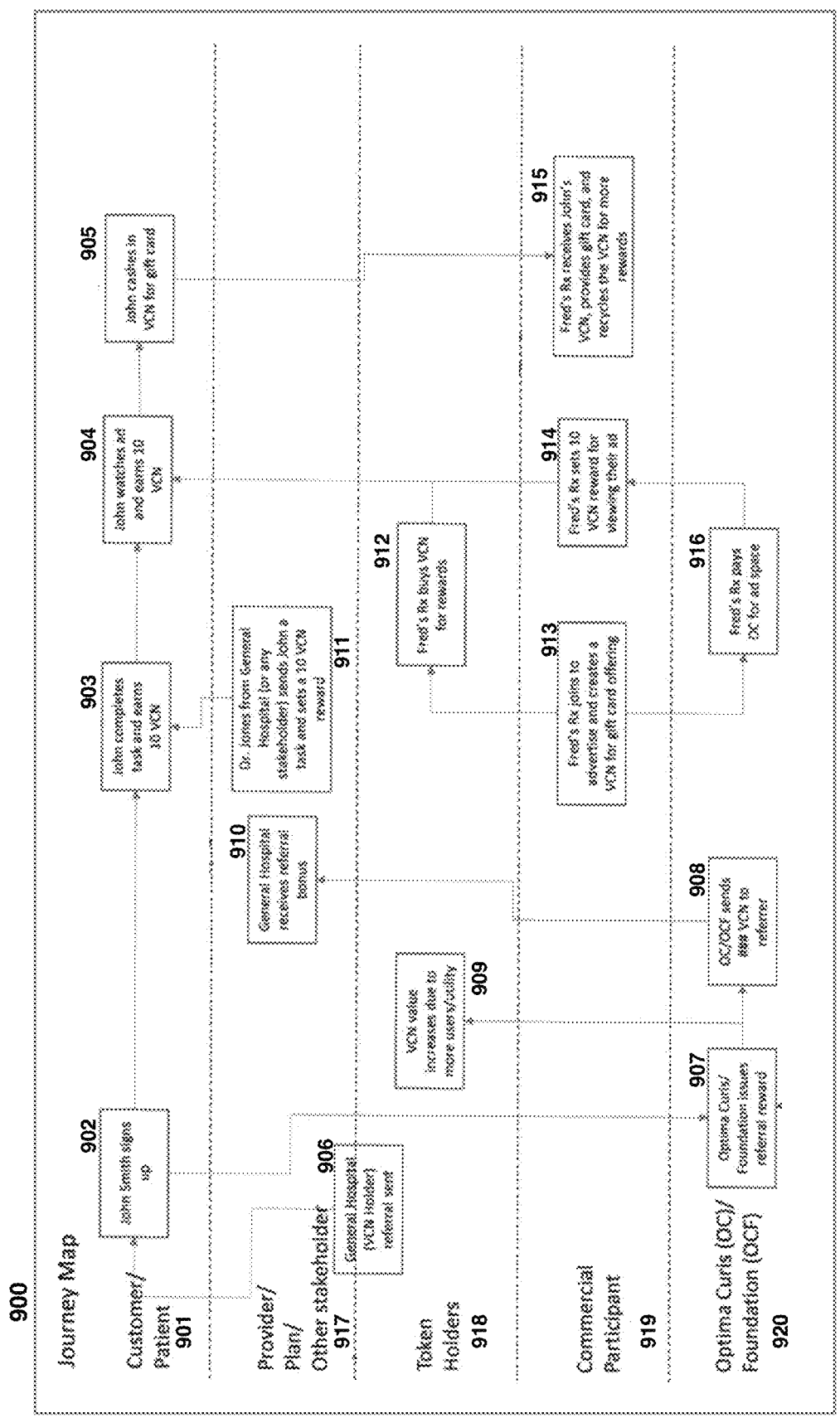
FIG. 9. depicts a block diagram illustrating one embodiment of the current invention.

FIG. 9, which is generally represented by the numeral 900 is an illustrative diagram showing the end to end process proposed by the present invention involving various Stakeholders. For example, communities made Consumers/Patients 901, Providers/Plan/Other Stakeholders 917, Token Holders 918, Commercial Participants 919, and other third party foundations 920 can all sign up on a decentralized platform or blockchain. A patient, for example John Smith, 902 can sign up from a referral provided by a token holder, such as a general hospital 906. For signing up, third parties can provide a reward 907. This in turn will raise the value of a reward token 909. Third parties can further determine the referrer 908 and provide them rewards 910 for involving additional patients.

Each time a patient completes a task, he/she will earn some value of tokens 903. These rewards can be further approved and supplemented by healthcare providers who have a vested interest in the patient's health 911. Moreover, third party advertisers can provide information and advertisements to the patient, who can view these advertisements in exchange for rewards 904. Third parties can further subsidize certain actions in the form of rewards, such as the purchase of certain brands of medicine 914. Specific third-party providers can pay for further ad space using a token 916 and can further incentivize the purchase of their products through gift cards 913 or virtual currency 912. Patients can further exchange the virtual currency for FIAT currency 905. Those tokens can be taken back into the system and used as further rewards 915.

In another embodiment, payers can track the average cost of healthcare by type and category of patient and make requests for recommendations for behavioral modifications for specific types of communities to the medical care community at large.

The social aspect of the present invention creates a community linking patients, caregivers and other stakeholders with the remainder their respective circles. In one embodiment, the circles have a secure method of conducting conversation, through direct messaging, requesting, text messaging, emailing, and other communication-based services. Moderated private communities are created alongside moderated public communities.

In another embodiment, the Caregivers are encouraged to provide patient specific recommendations with a reward. The reward engine can request specific behaviors for specific groups, patients can recommend behaviors, other caregivers can recommend behaviors, and they can be volunteered. The rewards engine can be configured to distribute rewards to successful recommendations, and successful actions.

In another embodiment, the entire connected network, which includes the health board, the patient, the provider of care, the payers, can be provided rewards based on predefined actions. A marketplace is available to the stakeholders to provide items that can help in behavior modification. These can range from fitness trackers, to dietary supplements.

In another embodiment, the marketplace itself can adjust prices and be modified based on a patient need. A caregiver, or payer, can subsidize items that will help improve the system.

In another embodiment, all payments and rewards are based on cryptocurrency. The network provides a method of holding the virtual currency through a "digital wallet."
In one embodiment, the rewards engine autonomously determines the value of a reward, the basis of the reward, the activity required for a reward, and distributes the reward. This information can be based on historical data, or predetermined by the payee network.

Stakeholders such as Healtchare Providers, Patients, Payers, Employers, Families, Caregivers, Advertisers, Marketplace participants, and any other members that participate in a distributed system are used synonymously. Any specific Stakeholder can be replaced by another Stakeholder without limitation, and are only described for informational purposes.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a non-transitory computer readable medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

The present technology requires a data processing system with sufficient memory and processing power to store and recall user data in real time. In addition, the invention may be implemented in a computer program for running on a computer system, at least including code portions for performing steps of a method according to the invention when run on a programmable apparatus, such as a computer system or enabling a programmable apparatus to perform functions of a device or system according to the invention. The computer program may cause the storage system to allocate disk drives to disk drive groups. In particular, the distributed decentralized network discussed herein must be capable of analyzing user and bid data in a manner that can optimize the bidding process.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that may be included in the disclosed technology. The disclosed technology is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the technology disclosed herein. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

While the present invention has been described with reference to one or more preferred embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention.

In the foregoing specification, the invention has been described with reference to specific examples of embodiments of the invention. It will, however, be evident that various modifications and changes may be made therein without departing from the broader spirit and scope of the invention as set forth in the appended claims.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

Any reference to "having", "including" or "comprising" should be applied mutatis mutandis to "consisting" and/or "consisting essentially of."

What is claimed is:

1. A method for promoting, maintaining and rewarding health and wellness, the method comprising:
   a network, the network comprising:
      a plurality of nodes, wherein each node in the plurality of nodes is configured to transact autonomously with at least two nodes in the plurality of nodes and configured to communicate with at least one server;
      the at least one server, the at least one server comprising at least one hardware processor, a non-transitory machine-readable storage medium having an executable computer readable program code, the at least one hardware processor configured to execute the computer-readable program code;
      the server, capable of identifying at least one account holder using a private key and a public key and connected to a rewards engine; and
      the rewards engine configured to categorize the at least one account holder, wherein each participating member of a healthcare network is rewarded for compliance with healthcare provider recommendations, and wherein said healthcare provider provides said recommendations directly to said participating member of a healthcare network via secure private communication, and wherein additional third-party payers participate in said network in response to guidance of said healthcare provider by marketing and selling healthy products corresponding with said healthcare provider recommendations by way of said network and each participating member is rewarded by any other network payer member by providing personal data to said network payer members and said payer members will be incentivized to participate in response to said payers tracking and implementing incentives to reduce healthcare costs and improve profitability of said network for the benefit of all members of said network.

2. The network of claim 1, wherein the at least one server is further configured to autonomously transact with the at least one account holder.

3. The network of claim 1, wherein a first account holder can be associated with at least one other account holder.

4. The rewards engine of claim 1, further capable of defining a reward amount.

5. The rewards engine of claim 1, capable of defining a rewardable behavior.

6. The at least one server of claim 1, configured to autonomously distribute a reward to least one account holder.

7. The server of claim 6, wherein the reward is in the form of FIAT currency.

8. The server of claim 6, wherein the reward is in the form of virtual currency.

9. The network of claim 1, further configured allow transactions on a virtual marketplace.

10. The marketplace of claim 9, further configured to accept virtual currency.

11. The marketplace of claim 9, configured to receive fiat currency.

12. The marketplace of claim 9, configured to autonomously adjust prices of specific items.

13. The network of claim 1, configured as a decentralized network.

14. The network of claim 1, configured as a distributed network.

15. The network of claim 1, configured a blockchain network.

16. A method for distributing rewards on a network, the method comprising:
a server, the server comprising at least one hardware processor, a non-transitory machine-readable storage medium, the server configured to:
receive at least one term governing the distribution of a reward, the digital address of the intended recipient of a reward, and a reward amount;
validate the completion of the at least one term governing the distribution of the reward; and
distributing the reward, wherein each participating member of a healthcare network is rewarded for compliance with healthcare provider recommendations, wherein said healthcare provider provides said healthcare provider recommendations directly to said participating member of a healthcare network securely and privately, and wherein additional third-party payers participate in said network in response to guidance of said healthcare provider by marketing and selling healthy products corresponding with said healthcare provider recommendations by way of said network and each participating member is rewarded by any other network payer member by providing personal data to said other network payer members and said payer members will be incentivized to participate in response to said payers tracking and implementing incentives to reduce healthcare costs and improve profitability of said network for the benefit of all members of said network.

17. The network of claim 16, further configured as a distributed network.

18. The network of claim 16, further configured as a blockchain network.

19. The network of claim 16, wherein the rewards are virtual currency.

20. The network of claim 16, wherein the rewards are fiat currency.

21. The server of claim 20, capable of analyzing and storing information regarding the at least two stakeholders.

22. The network of claim 20, wherein each of the at least two stakeholders can define the terms governing the distribution of the reward.

23. The network of claim 20, wherein each of the at least two stakeholders can define the amount of the reward.

24. The server of claim 16, capable of registering a user account for at least two stakeholders wherein said server further is capable of allowing communication between the at least two stakeholders.

25. The network of claim 16, wherein the reward is distributed to a digital wallet.

26. The network of claim 16, further connected to a virtual marketplace.

27. The virtual marketplace of claim 25, wherein the price of an item is autonomously adjusted.

28. A decentralized network for autonomously distributing rewards, the decentralized network comprising:
At least one hardware processor, a non-transitory machine-readable storage medium having an executable computer readable program code, the at least one hardware processor configured to execute the computer-readable program code to:
receive an executable smart contract;
the smart contract containing at least one term governing the distribution of a reward, a reward amount, and an address of the intended recipient of the reward;
receive a request to validate the completion of the at least one term of the smart contract,
validate the completion of the at least one term of smart contract; transfer the reward amount to the distribution address; and update a ledger with the distribution information, wherein each participating member of a healthcare network is rewarded for compliance with healthcare provider recommendations, and wherein said healthcare provider recommendations are provided directly to said participating member of a healthcare network in a secure private manner associated with private records attributed to said participating member if a healthcare network, and wherein additional third-party payers participate in said network in response to guidance of said healthcare provider by marketing and selling healthy products corresponding with said healthcare provider recommendations by way of said network and each participating member is rewarded by any other network payer member by providing personal data to said other network payer member and said payer member will be incentivized to participate in response to said payers tracking and implementing incentives to reduce healthcare costs and improve profitability of said network for the benefit of all members of said network.

29. The decentralized network of claim 28, wherein the at least one term governing the distribution of a reward is defined by at least one end user.

30. The decentralized network of claim 28, wherein the at least one term governing the distribution of a reward is autonomously determined based on publicly available information.

31. The decentralized network of claim 28, wherein the reward value is defined by at least one end user.

32. The decentralized network of claim 28, wherein the reward value is autonomously determined.

33. The decentralized network of claim 28, wherein the at least one term governing the distribution of a reward requests the recipient of the reward to make a behavioral change.

34. The decentralized network of claim 28, wherein the at least one term governing the distribution of a reward requests the recipient of the reward to make a lifestyle change.

35. The decentralized network of claim 28, wherein the at least one term governing the distribution of a reward requests the recipient of the reward to make a psychological change.

36. The decentralized network of claim 28, wherein the at least one term governing the distribution of a reward requests the recipient of the reward to make a health change.

37. The decentralized network of claim 28, wherein the at least one term governing the distribution of a reward requests the recipient of the reward to implement some form of preventative medicine.

38. The decentralized network of claim 28, wherein the at least one term governing the distribution of a reward requests the recipient review third party advertisements.

39. The decentralized network of claim 28, wherein the validation of the at least on term governing the distribution of a reward is based on data provided from a wearable device.

40. The decentralized network of claim 28, wherein the reward is FIAT currency.

41. The decentralized network of claim 28, wherein the reward is virtual currency tokens.

42. The decentralized network of claim 28, wherein the rewards can be used to purchase items in a virtual marketplace.

43. The decentralized network of claim 28, wherein the reward is a discount for an item in a virtual marketplace.

* * * * *